(12) United States Patent  
Ghareeb

(10) Patent No.: US 7,488,333 B2
(45) Date of Patent: Feb. 10, 2009

(54) DEVICE FOR ENABLING THE TREATMENT OF HEMORRHOIDS

(76) Inventor: Essam Mohamed Ghareeb, Glandore, Rossfad, Ballinamallard, Co. Fermanagh (GB) BT942LS ( * ) Notice: Subject to any disclaimer, the term of this patent is extended or adjusted under 35 U.S.C. 154(b) by 716 days.

(21) Appl. No.: 10/515,457

(22) PCT Filed: May 22, 2003

(86) PCT No.: PCT/IB03/02669

§ 371 (c)(1),
(2), (4) Date: Feb. 15, 2005

(87) PCT Pub. No.: WO03/099141

PCT Pub. Date: Dec. 4, 2003

(65) Prior Publication Data
US 2005/0143757 A1 Jun. 30, 2005

(30) Foreign Application Priority Data
May 25, 2002 (GB) ................................ 0212125.9

(51) Int. Cl.
*A61B 17/10* (2006.01)
*A61B 1/00* (2006.01)
(52) U.S. Cl. ...................................... 606/140; 600/104
(58) Field of Classification Search ................. 606/139, 606/140, 144, 164, 165, 171; 604/534; 600/104
See application file for complete search history.

(56) References Cited

U.S. PATENT DOCUMENTS

| 4,226,239 A | * | 10/1980 | Polk et al. ................... 606/141 |
| 4,493,319 A | * | 1/1985 | Polk et al. ................... 606/141 |
| 5,681,328 A | | 10/1997 | Lamport et al. |
| 5,788,715 A | * | 8/1998 | Watson et al. ............... 606/140 |

FOREIGN PATENT DOCUMENTS

| DE | G 92 05 453.6 | 7/1992 |
| EP | 95302722.4 | 2/1995 |
| WO | PCT/US94/11829 | 5/1995 |
| WO | PCT/SE99/01259 | 1/2000 |

* cited by examiner

*Primary Examiner*—Julian W Woo
*Assistant Examiner*—Victor X Nguyen
(74) *Attorney, Agent, or Firm*—Michael P. Mazza

(57) ABSTRACT

A ligating device for applying successive elastic bands 18 to tissue 54. In one preferred embodiment, the device includes a barrel having an opening into which the tissue can be drawn and a plurality of circumferential grooves 52 around the barrel each for accommodating a respective ligating band. The grooves may be defined by ridges 24, 30 on first and second coaxial tubes 20, 22 respectively, the second tube 22 being reciprocal relative to the first tube 20 so that when the second tube 22 advances towards the free end of the barrel its ridges 30 push the bands 18 forwardly so that they ride up over the ridges 24 of the first tube 20 to each lie one groove nearer the free end, the foremost band 18a being pushed off the free end of the first tube onto the tissue. When the second tube 22 retracts away from the free end the bands 18 ride up over the ridges 30 of the second tube to remain in their advanced position.

6 Claims, 6 Drawing Sheets

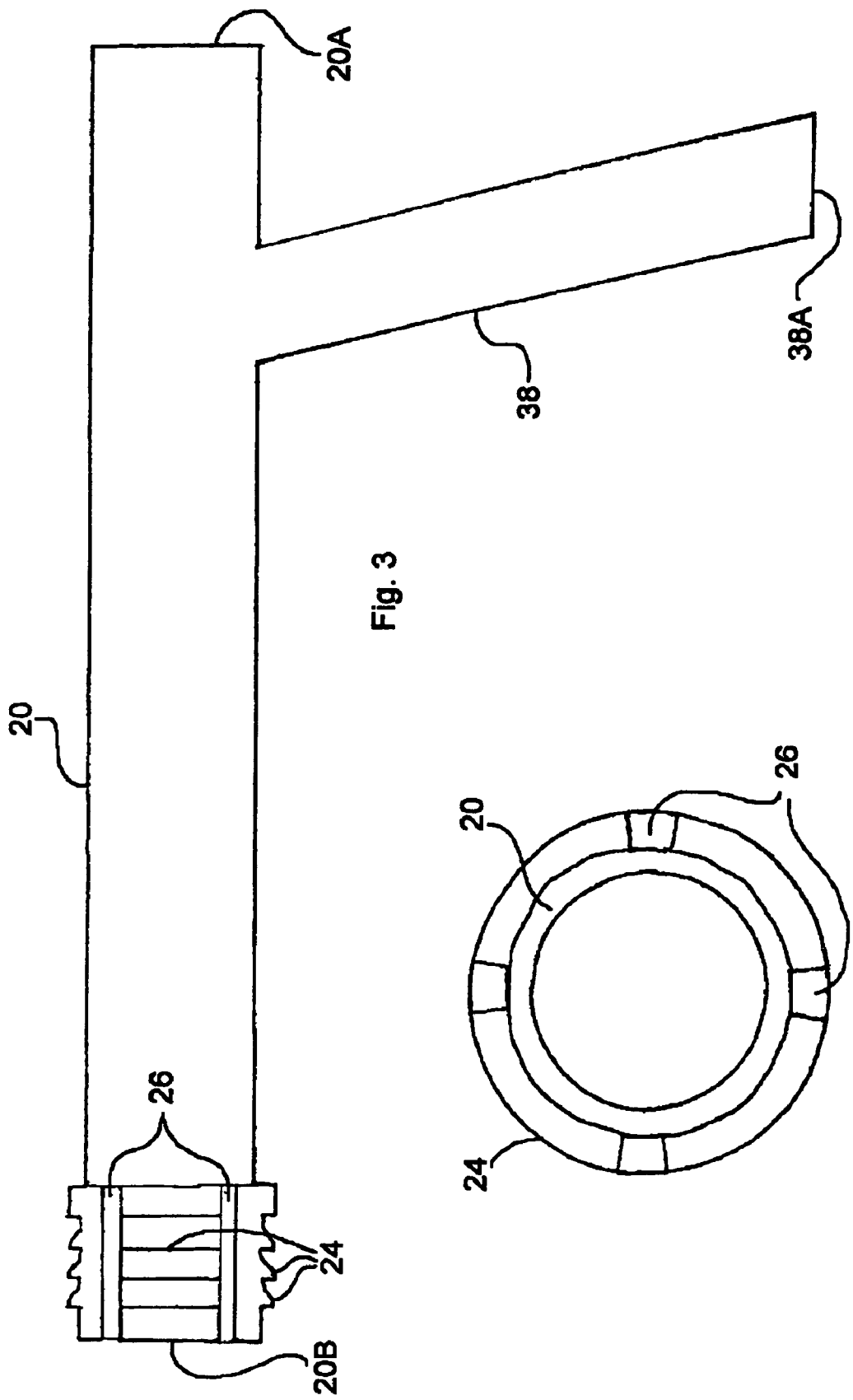

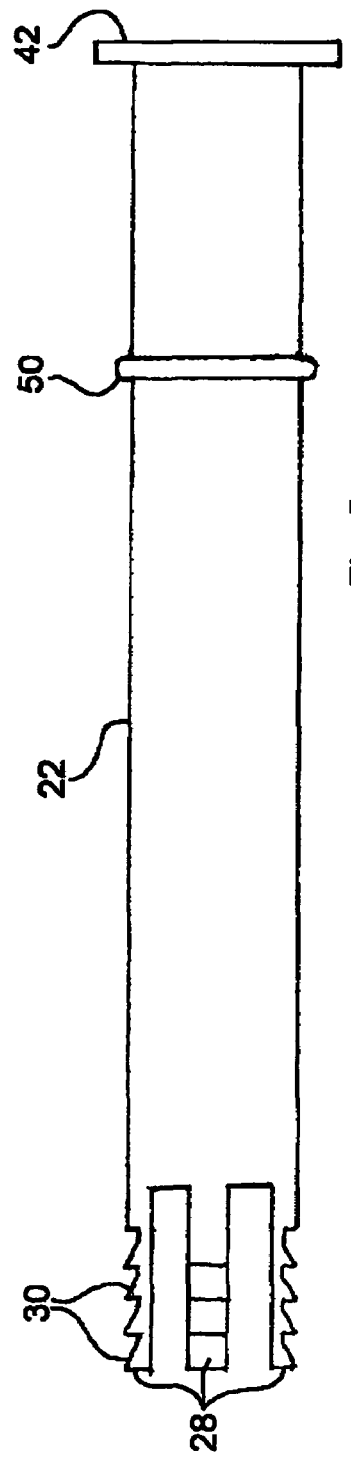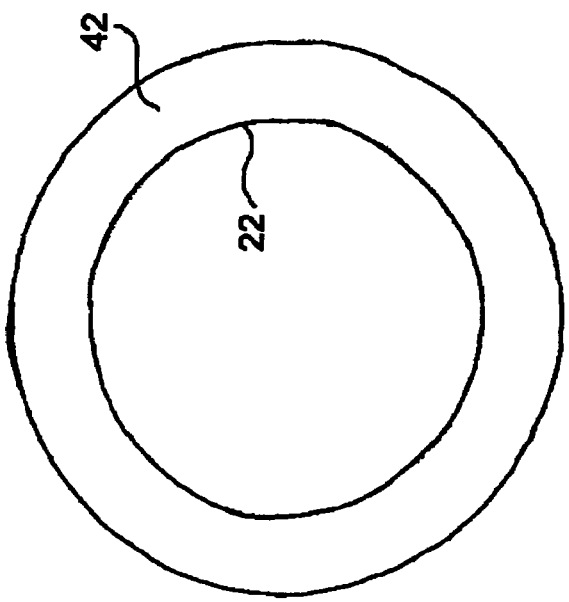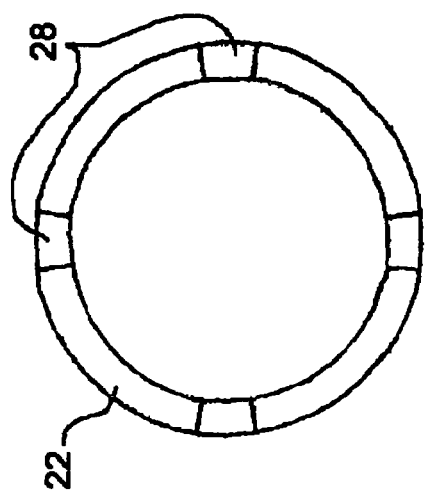

DEVICE FOR ENABLING THE TREATMENT OF HEMORRHOIDS

CONTINUATION INFORMATION

This application claims priority from PCT International Application No. PCT/IBO3/02669, filed May 22, 2003, which claims priority from Great Britain patent application No. 0212125.9, filed May 25, 2002.

BACKGROUND OF THE INVENTION

The invention is related to a device for the application of resilient ligating bands around tissues for the treatment of conditions such as, but not limited to, hemorrhoids (piles).

Hemorrhoids are one of the most common surgical diseases around the world. Depending on their severity, which is graded from 1st-4th degrees, they can be treated on an out-patient basis. Various methods of treatment were developed. Infrared coagulation, radio frequency coagulation, direct current coagulation, rubber band ligation, sclerotherapy, cryosurgery, laser surgery and scalpel surgery.

The lease expensive and most widely used method is rubber band ligation. This is suitable for the great majority of cases. It has been in use for many years and has proved to be the most effective.

In the known technique, a relatively long forceps is employed to hold the hemorrhoid, which is pulled through an o-ring forceps with a relatively long arm. The external part of the o-ring holds an already stretched rubber band. Once the forceps has grasped the hemorrhoid, the rubber band is fired from the o-ring by a simple pushing mechanism. The problems with the known technique include the requirement for two people to perform it, one to hold the anoscope and the other to apply the bands. This anoscope is needed to be able to visualize the hemorrhoids.

Because it is necessary to have two people to perform the technique, misfiring of the bands is frequent and readjustment is therefore required. Sterilization of the equipment between patients is essential, so many sets are needed.

As each patient usually needs 2-3 rubber bands to be applied, the o-ring must be loaded each time with a fresh band, which is a demanding task. Thus the o-ring forceps must be removed while maintaining the anoscope inside the patient, as it is painful to remove and then reinsert it.

A less common condition called oesoghageal varices, which is dilated veins at the lower part of the oesophagus, is treated in a similar way by applying rubber bands to the varices.

This treatment has proved its efficiency in stopping bleeding from oesophageal varices. The rubber bands are loaded on a cartridge, which is loaded on the tip of a flexible fibre optic gastroscope. This is passed down into the patients' oesophagus and the rubber bands are applied on the varices, which are drawn into the cartridge by the means of suction. The mechanisms used to fire the rubber bands are dependent on a thread applied over the cartridge body, under the rubber bands. Drawing the thread will fire the rubber bands. A plurality of rubber bands can be fired using this method.

The problem with this method is that time and a complex effort are needed to assemble the cartridges. That makes them expensive. The same mechanism is not used widely to treat hemorrhoids because the cartridge needs to be applied on a long fibre optic scope and it has proved to be too expensive to use for a very common condition as hemorrhoids.

It is an object of this invention to provide a device that will enable one person to apply several elastic bands (or other resilient ligating bands) onto hemorrhoids or other tissue such as oesophageal varices without the need to recharge the device by applying more bands each time an application is required.

SUMMARY OF THE INVENTION

The present invention overcomes disadvantages of prior devices for treating conditions such as hemorrhoids and provides new advantages.

In a preferred embodiment, a device is provided for applying successive resilient ligating bands to tissue. The device includes a barrel having an opening at a free end thereof, a mechanism and/or process for drawing tissue to be ligated into the opening, and a plurality of circumferential grooves around the barrel adjacent the free end each for accommodating a respective ligating band. The grooves may be defined by ridges on two separate components of the barrel. A first component of the barrel may be reciprocal relative to the second component in the direction towards and away from the free end of the barrel so that when the first component advances towards the free end, its ridges push the bands forwardly so that they ride up over the ridges of the second component to each lie one groove nearer the free end. In this embodiment, the foremost band may be pushed off the free end of the second component onto the tissue, whereas when the first component retracts away from the free end the bands may ride up over the ridges of the first component to remain in their advanced positions.

In a particularly preferred embodiment, the first component may include a tube having at its free end a plurality of circumferential ridges interrupted by paraxial slots. The second component may include a second tube coaxially surrounding and slidable on the first tube. The second component may also include a plurality of fingers which are slidably accommodated in the slots of the first component. Also, the fingers may have ridges with substantially the same pitch and cross-section as those of the first component. As one non-limiting example, the ridges may have a sawtooth cross-section inclined in the direction towards the free end of the barrel.

Preferably, the means for drawing the hemorrhoid into the opening may include means for establishing a reduced air pressure in the opening via the first tube.

In another embodiment, the second component may be resiliently biased away from the free end of the barrel against a stop means, and may be advanced towards the free end of the barrel against the resilient bias by a manual actuator. The resilient bias may return the second component to the stop means when the manual actuator is released.

BRIEF DESCRIPTION OF THE DRAWINGS

The novel features which are characteristic of the invention are set forth in the appended claims. The invention itself, however, together with further objects and attendant advantages thereof, will be best understood by reference to the following description taken in connection with the accompanying drawings, which show a preferred embodiment by way of example only, in which:

FIG. 3 is a side view of the fixed (inner) tube of the barrel which forms one component of the band-firing mechanism and which transmits the vacuum through the device;

FIG. 4 is the front elevation of the tube of FIG. 3;

FIG. 5 is a side view of the reciprocating (outer) tube which forms the other component of the band-firing mechanism;

FIG. 6 is the front elevation of the tube of FIG. 5;

FIG. 7 is the back elevation of the tube of FIG. 5;

DETAILED DESCRIPTION OF THE PREFERRED EMBODIMENTS

Figure 1:
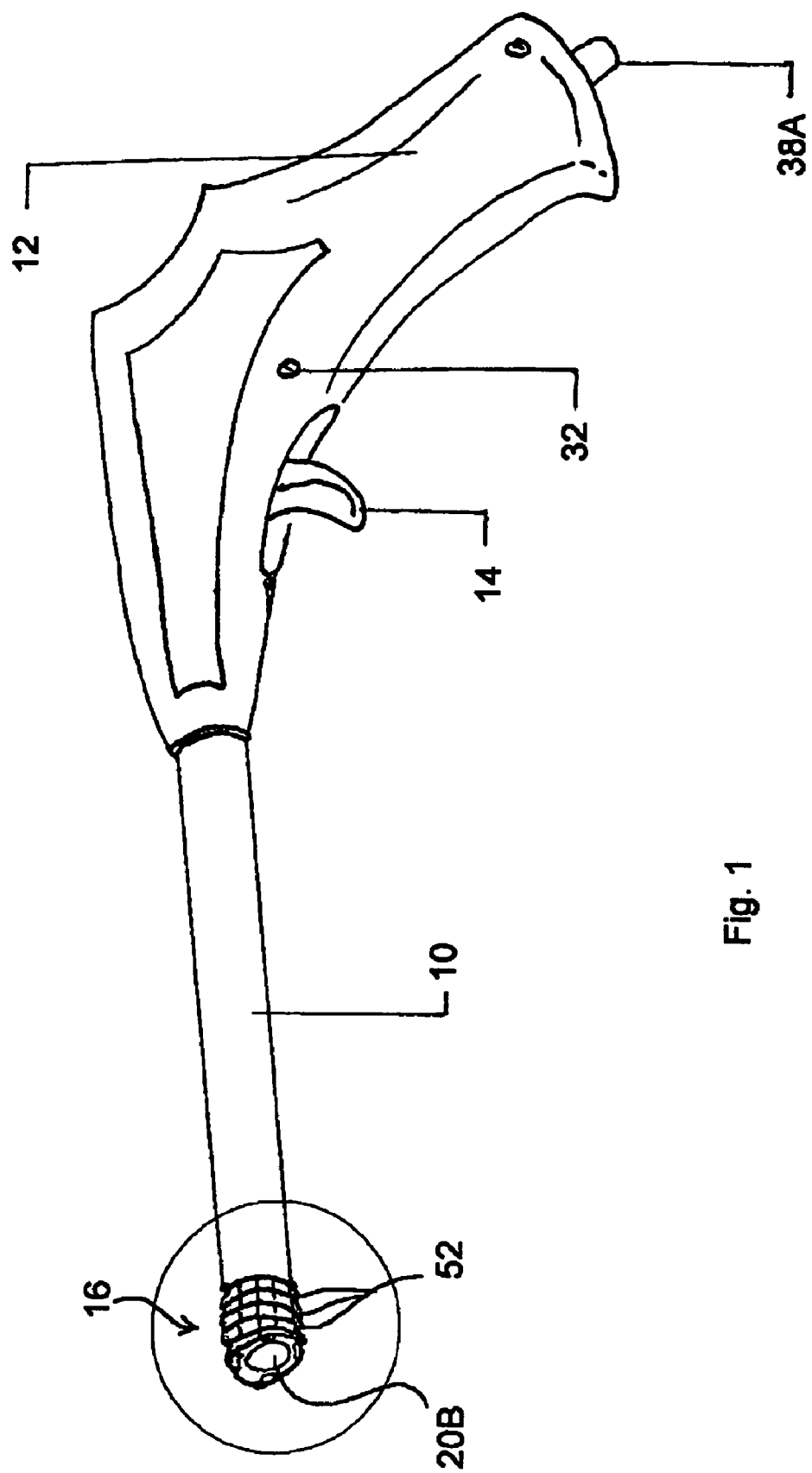
FIG. 1 is a perspective view of a device according to the invention.

Set forth below is a description of what are believed to be the preferred embodiments and/or best examples of the invention claimed. Future and present alternatives and modifications to this preferred embodiment are contemplated. Any alternatives or modifications which make insubstantial changes in function, in purpose, in structure, or in result are intended to be covered by the claims of this patent.

In accordance with a preferred embodiment of the invention, a device is provided for applying successive resilient ligating bands to tissue, the device comprising a barrel having an opening at a free end thereof, means for drawing tissue to be ligated into the opening, and a plurality of circumferential grooves around the barrel adjacent the free end each for accommodating a respective ligating band, the grooves being defined by ridges on two separate components of the barrel of which a first component is reciprocal relative to the second component in the direction towards and away from the free end of the barrel so that when the first component advances towards the free end its ridges push the bands forwardly so that they ride up over the ridges of the second component to each lie one groove nearer the free end, the foremost band being pushed off the free end of the second component onto the tissue, whereas when the first component retracts away from the free end the bands ride up over the ridges of the first component to remain in their advanced positions.

Referring now to the drawings, the device is generally in the shape of a pistol having a barrel 10, a piston-grip type handle 12 and a trigger 14. The barrel 10 has a mechanism 16 (see also FIG. 8 and 9) for applying successive elastic bands 18 (or other resilient ligating bands) off the free front end of the barrel onto tissue 54 to be ligated.

The barrel comprises inner and outer coaxial hollow tubes 20, 22 respectively, the inner tube 20 being fixed relative to the handle 12 and the outer tube 22 being a close sliding fit on the inner tube 20 for reciprocation towards and away from the free end of the barrel. The free end of the inner tube 20 has a plurality of circumferential ridges 24 of substantially the same diameter, interrupted at 90 degree intervals by relatively narrow paraxial slots 26 (i.e. slots parallel to the axis of the tube). The ridges 24 have a sawtooth cross-section inclined upwardly at an angle of about 15 degrees in the direction towards the free and of the barrel 10. The free end of the outer tube 22 has four equiangularly spaced fingers 28 which, when the tube 22 is assembled on the tube 20, are slidably located in the slots 26 in the free end of the inner tube 20 (FIGS. 8 and 9). The fingers 28 have ridges 30 with substantially the same pitch and cross-section as the ridges 24 of the tube 20.

Figure 2:
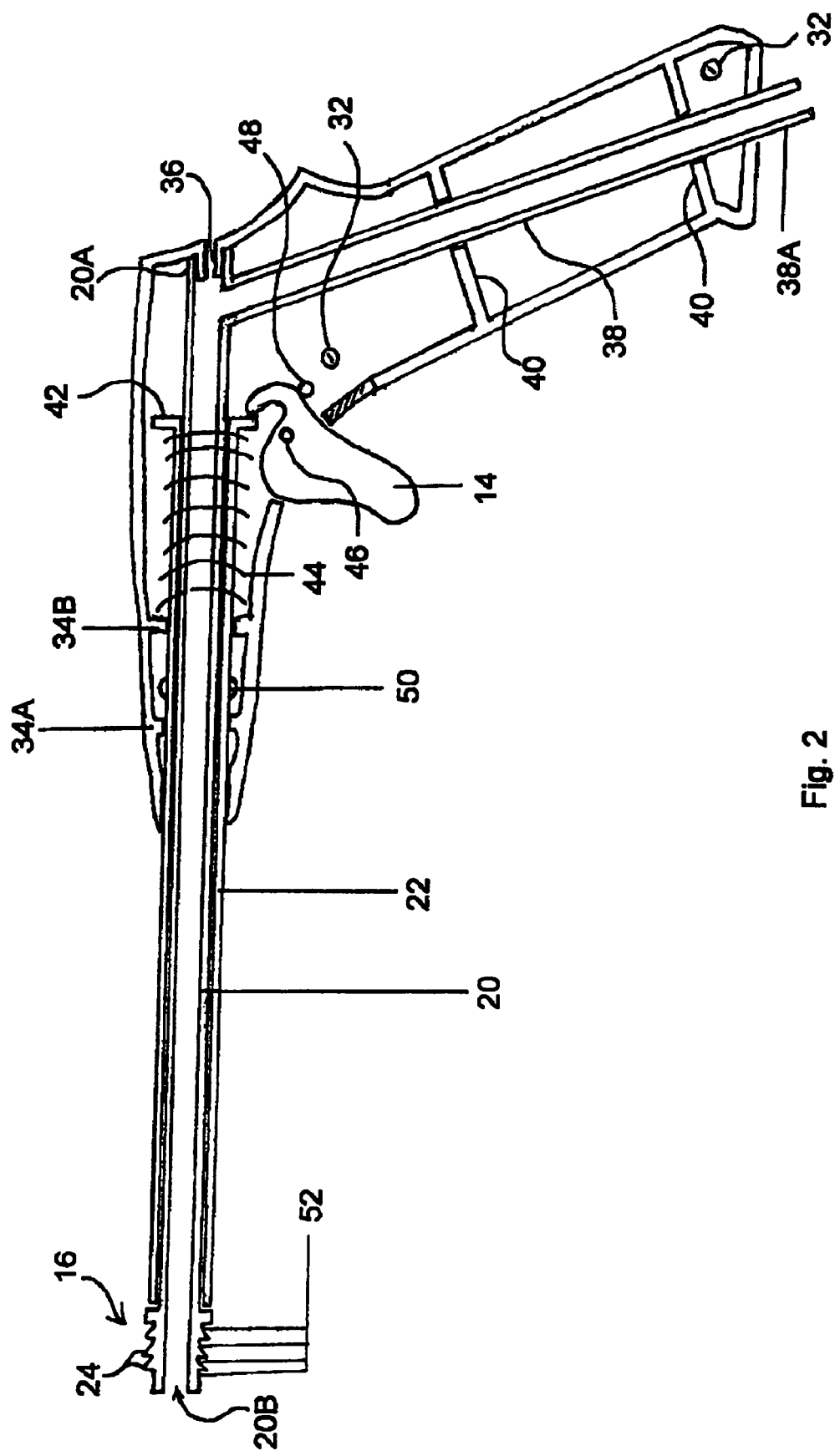
FIG. 2 is a longitudinal cross-section of the device of FIG. 1.

The handle 12 is made of two substantially mirror image halves, of which the right hand half is shown in FIG. 2, the two halves being screwed together by screws 32 in conventional manner. The barrel 10 is mounted in the handle in the following manner. The outer tube 22 is located in the handle 12 between annular collars 34A, 34B which snugly embrace the tube 22 but allow it to slide along its own axis. The inner tube 20 extends through the outer tube 22 and has an open rear end 20A which extends over and is fixed in airtight manner to a short, inwardly directed tubular stub 36 at the rear of the handle 12. The inner tube 20 also has a lateral branch 38 whose free open end 38A is exposed at the base of the handle 12 to allow a source of vacuum to be connected to the tube 20. The lateral branch 38 is supported by further annular collars 40 in the handle. Thus the inner tube 20 is fixed within the handle 12, whereas the outer tube 22 can slide on the tube 20 within defined limits now to be described.

The outer tube 22 has an annular flange 42 at is rear end, and a compression spring 44 acting between the collar 34B and the flange 42 resiliently biases the tube 22 away from the free end of the barrel, i.e. further into the handle 12. However, as seen in FIG. 2, the flange 42 bears against an extension of the trigger 14 so that the trigger is rotated clockwise (as seen in FIG. 2) about its axis 46 by the spring 44 acting via the flange 42. A stop member 48 in the handle limits the clockwise rotation of the trigger 14 and therefore the trigger 14, when abutting the member 48, effectively acts as a stop member for the tube 22 and defines one end of its range of sliding movement. The other end of the range of sliding movement of the tube 22 is defined by a circumferential collar 50 on the tube abutting the collar 34A in the handle.

The normal position of the outer tube 22, herein referred to as its retracted position, is as shown in FIG. 3, where the spring 44 biases the tube into the handle 12 and the flange 42 is stopped against the trigger 46. However, by pulling on the trigger 46 the latter may be rotated anti-clockwise against the bias of the spring 44 to slide the tube 22 forwardly on the tube 20 until the collar 50 comes up against the collar 34A. This position is referred to herein as the extended position of the tube 22. Of course, when the trigger 42 is released, the spring 44 returns the tube 22 to its retracted position.

Figure 8A:
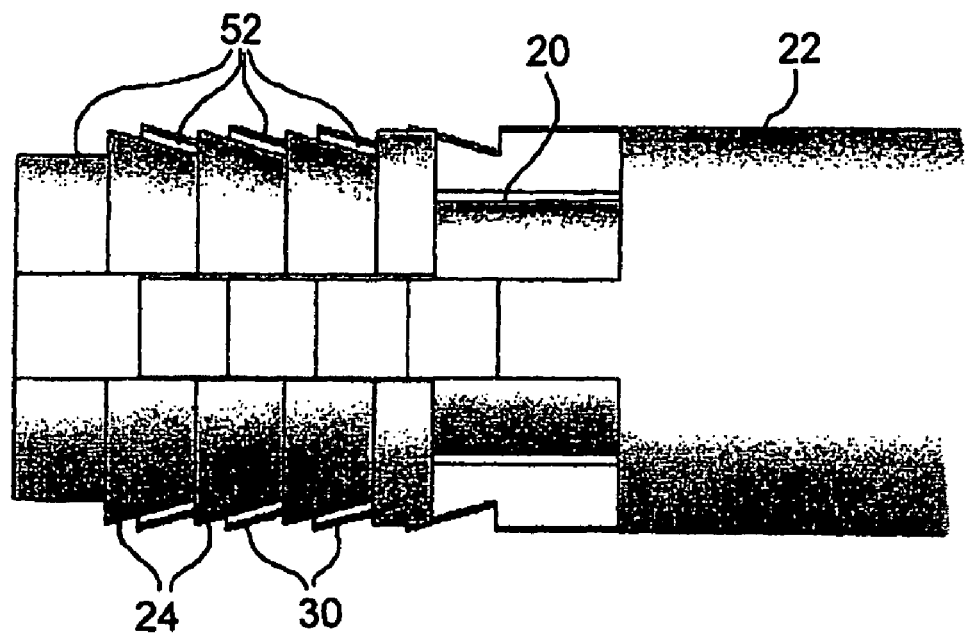
FIGS. 8(a) and 8(b) are enlarged side views illustrating the construction and operation of the elastic band applying mechanism at the free front end of the barrel shown circled in FIG. 1.
Figure 8B:
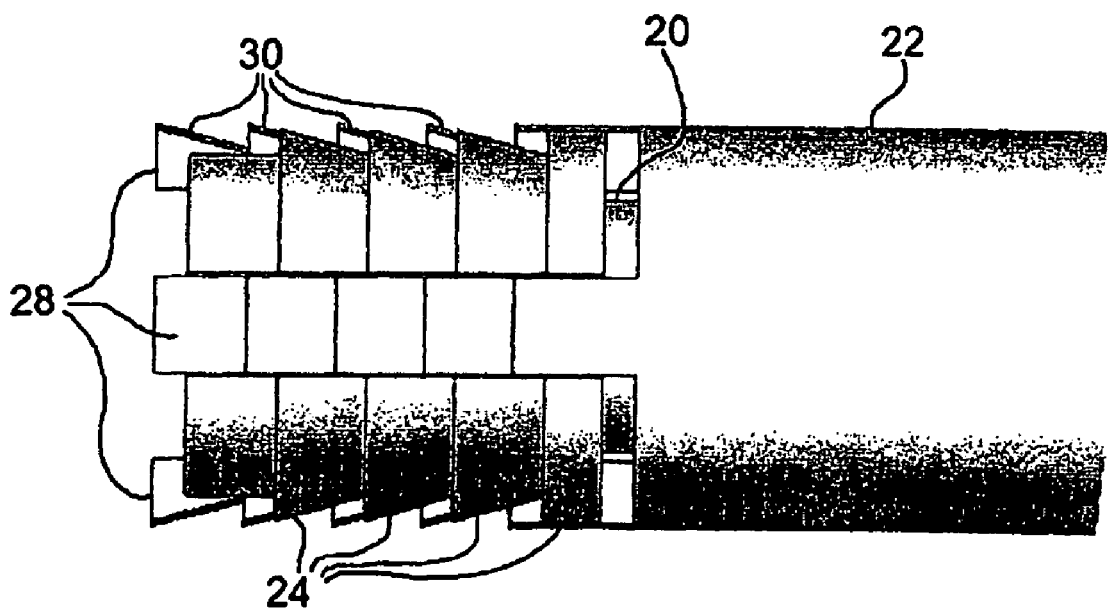
Figure 9A:
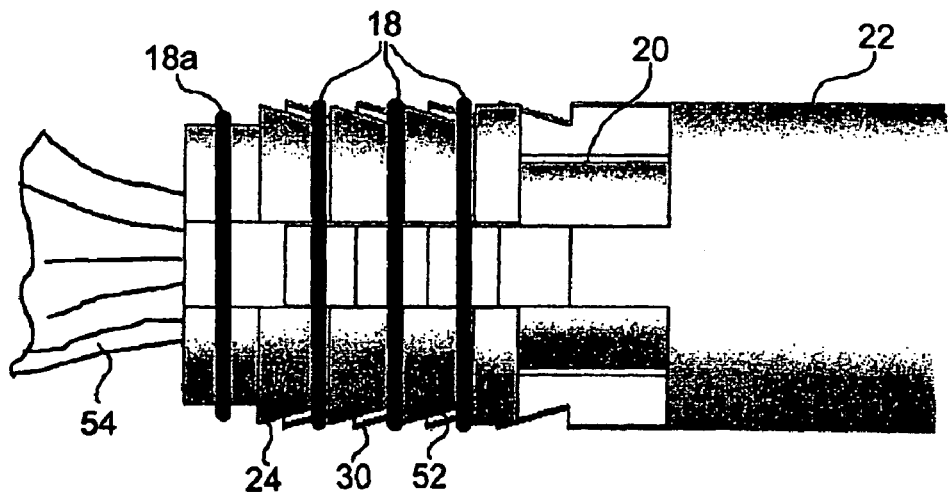
FIGS. 9(a) to 9(c) are views similar to those of FIGS. 8(a) and 8(b) but showing the mechanism in use.

Referring now in particular to FIG. 8, when the outer tube is in its retracted position, FIG. 8(a), the ridges 24 and 30 are approximately aligned to define a plurality of circumferential grooves 52 of substantially the same diameter, each for accommodating a respective elastic band 18 stretched around it, FIG. 9(a). As can be seen, to allow for tolerances in manufacture and deformation of parts in use, in the retracted position of the tube 22 the ridges 30 are slightly to the rear of the ridges 24, but not sufficiently to block or interrupt the grooves 52. When the outer tube is in its extended position, FIG. 8(b), the ridges 30 have moved forwardly by a distance greater than the pitch of the ridges 24.

The device may be used as follows. First, FIG. 9(a), rubber bands 18, or bands of other resilient material suitable for ligation, are stretched around respective grooves 52 by manual or other means while the tube 22 is in its retracted position. Next a vacuum is connected to the end 38A of the tube 20 and the free end of the barrel 10 is introduced into the anus through the use of an anoscope to treat, for example, hemorrhoids. One hand holds the anoscope, while the other holds the device. After identifying the hemorrhoid or other tissue 54, the thumb is applied to the external hole of the tubular stub 36 so the vacuum is transmitted to the hemorrhoid via the tube 20, after the free end of the barrel 10 is gently pressed against it. The hemorrhoid 54 will be drawn into the front opening 20B of the tube 20.

Figure 9B:
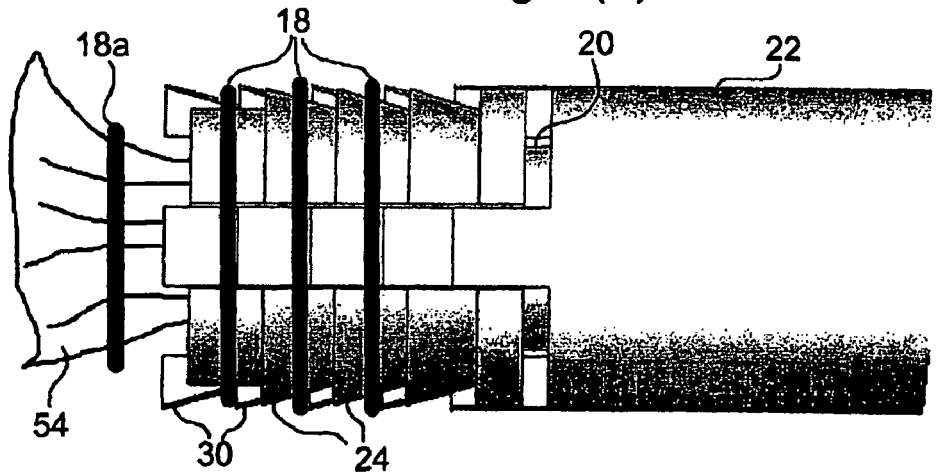
Figure 9C:
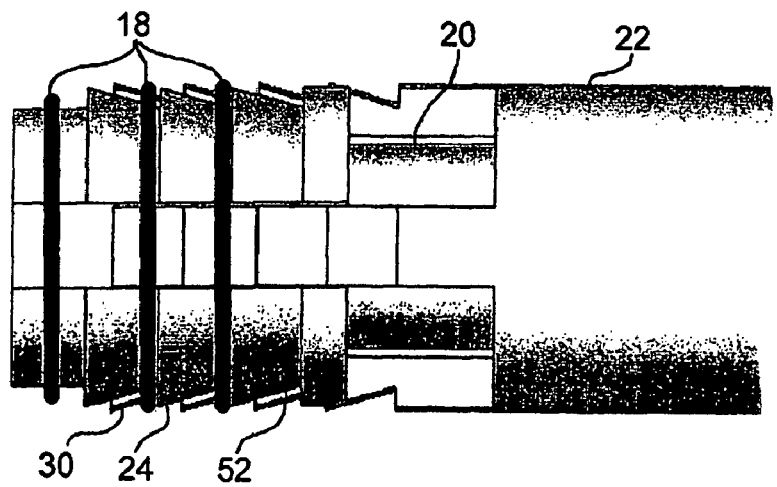

Now the trigger 14 is pressed to advance the tube 22 to its extended position. FIG. 9(b). As a result, each band 18 is pushed forwardly by the advancing ridges 30 to ride up over the stationary ridge 24 in front of it and at the same time the foremost elastic band, here designated 18a, is pushed off the free end of the tube 20 onto the tissue 54. On releasing the trigger 14, the spring 44 will return the sliding outer tube 22 back to its initial retracted position, FIG. 9(*c*). During the return movement of the tube 22 the remaining bands 18 ride up over the ridges 30 to settle back in the grooves 52, the bands 18 now each lying one groove 52 nearer the free end of the barrel. If another hemorrhoid needs to be treated, the procedure is repeated for the number of the bands on the tip of the barrel, without the need to withdraw the device from the anus.

Although the ridges 24 and 30 are shown as having a sawtooth cross-section, they can have a different cross-section provided it is possible to advance the bands step-by-step in the manner described. Also, the number of ridges, and hence the number of bands which can be accommodated by the device, can be more or less than that shown.

Other changes and modifications constituting insubstantial differences from the present invention, such as those expressed here or others left unexpressed but apparent to those of ordinary skill in the art, may be made without departing from the spirit and scope of the present invention and without diminishing its attendant advantages. It is, therefore, intended that such changes and modifications be covered by the following claims.

I claim:

1. A device for applying successive resilient ligating bands to tissue, the device comprising a barrel having an opening at a free end thereof, means for drawing tissue to be ligated into the opening, and a plurality of circumferential grooves around the barrel adjacent the free end each for accommodating a respective ligating band, the grooves being defined by ridges on two separate components of the barrel of which a first component is reciprocal relative to the second component in the direction towards and away from the free end of the barrel so that when the first component advances towards the free end its ridges push the bands forwardly so that they ride up over the ridges of the second component to each lie one groove nearer the free end, the foremost band being pushed off the free end of the second component onto the tissue, whereas when the first component retracts away from the free end the bands ride up over the ridges of the first component to remain in their advanced positions; and wherein the first component comprises a tube having at its free end a plurality of circumferential ridges interrupted by paraxial slots, and wherein the second component comprises a plurality of fingers which are slidably accommodated in the slots of the first component, the fingers having ridges with substantially the same pitch and cross-section as those of the first component.

2. A device as claimed in claim 1, wherein the ridges have a sawtooth cross-section inclined in the direction towards the free end of the barrel.

3. A device as claimed in claim 1, wherein the second component comprises a second tube coaxially surrounding and slidable on the first tube.

4. A device as claimed in claim 1, wherein the means for drawing tissue into the opening comprises mean for establishing a reduced air pressure in the opening via the first tube.

5. A device as claimed in claim 4, wherein the tissue comprises a hemorrhoid.

6. A device as claimed in claim 1, wherein the second component is resiliently biased away from the free end of the barrel against a stop means and may be advanced towards the free end of the barrel against the resilient bias by a manual actuator, the resilient bias returning the second component to the stop means when the manual actuator is released.

* * * * *